(12) United States Patent  
Solotoff

(10) Patent No.: US 12,064,049 B1
(45) Date of Patent: Aug. 20, 2024

(54) ADJUSTABLE COMFORT PILLOW

(71) Applicant: PREFERRED PRESCRIPTION INC., Hollywood, FL (US)

(72) Inventor: Brandon Solotoff, Boca Raton, FL (US)

(73) Assignee: Preferred Perscription INC., Hollywood, FL (US)

( * ) Notice: Subject to any disclaimer, the term of this patent is extended or adjusted under 35 U.S.C. 154(b) by 511 days.

(21) Appl. No.: 16/986,603

(22) Filed: Aug. 6, 2020

Related U.S. Application Data

(63) Continuation-in-part of application No. 16/254,790, filed on Jan. 23, 2019, now abandoned.

(60) Provisional application No. 62/898,606, filed on Sep. 11, 2019, provisional application No. 62/884,263, (Continued)

(51) Int. Cl.
| | | |
|---|---|---|
| *A47G 9/10* | (2006.01) | |
| *A61B 5/00* | (2006.01) | |
| *A61B 7/00* | (2006.01) | |
| *A61F 5/56* | (2006.01) | |

(52) U.S. Cl.
CPC .......... *A47G 9/1027* (2013.01); *A47G 9/1045* (2013.01); *A61B 5/4818* (2013.01); *A61B 5/4836* (2013.01); *A61B 7/003* (2013.01); *A61F 5/56* (2013.01); *A47G 2009/1018* (2013.01)

(58) Field of Classification Search
CPC ................ A47G 9/1027; A47G 9/1045; A47G 2009/1018; A47G 9/109; A47G 9/102; A61B 5/4818; A61B 5/4836; A61B 7/003; A61F 5/56; A47C 27/08; A47C 27/081; A47C 27/082; A47C 27/083; A47C 27/088

See application file for complete search history.

(56) References Cited

U.S. PATENT DOCUMENTS

| | | | |
|---|---|---|---|
| 2,682,918 A | | 7/1954 | Porter |
| 2,691,179 A | | 10/1954 | Kann |
| 3,298,044 A | | 1/1967 | Saltness |

(Continued)

FOREIGN PATENT DOCUMENTS

| | | | | |
|---|---|---|---|---|
| CN | 201398755 Y | * | 2/2010 | |
| CN | 201929541 U | * | 8/2011 | |

(Continued)

*Primary Examiner* — Eric J Kurilla
*Assistant Examiner* — Amanda L Bailey
(74) *Attorney, Agent, or Firm* — Thomas A. O'Rourke; James Bongiorno; O'Rourke IP Law P.L.L.C.

(57) ABSTRACT

An adjustable pillow includes: upper and lower layers of foam, and first and second end caps of foam joined together and form a cavity. A plurality of individually inflatable bladders are positioned in the cavity of foam, and each has the same size and shape. A respective tube is in fluid communication with each of the plurality of individually inflatable bladders and with a pump that is configured to inflate any one or more of the plurality of individually inflatable bladders sequentially to a particular pressure, to inflate the adjustable pillow to a desired height selected by a user. A processor, electronic circuitry, and one or more voice activated microphones coupled to the processor and electronic circuitry receive and detect snoring sounds made by a user, with the processor configured to actuate one valves and/or pump to adjust the inflation until the detected snoring sounds falls below a threshold level.

17 Claims, 16 Drawing Sheets

Related U.S. Application Data filed on Aug. 8, 2019, provisional application No. 62/621,733, filed on Jan. 25, 2018.

(56) References Cited

U.S. PATENT DOCUMENTS

| | | | |
|---|---|---|---|
| 3,303,518 A | 2/1967 | Ingram | |
| 3,568,227 A | 3/1971 | Dunham | |
| 3,644,949 A | 2/1972 | Diamond | |
| 4,389,742 A | 6/1983 | DeWitt | |
| 5,708,999 A | 1/1998 | Priolo | |
| 5,771,514 A | 6/1998 | Wilhoit | |
| 6,510,573 B1 | 1/2003 | Grabe | |
| 6,622,326 B2 | 9/2003 | Richardson | |
| 6,934,989 B2 | 8/2005 | Ledvina | |
| 6,951,038 B1 * | 10/2005 | Ganoe, Sr. | A47G 9/1027 |
| | | | 5/636 |
| 7,146,665 B1 | 12/2006 | Moorin | |
| 7,444,697 B2 | 11/2008 | Williams | |
| 7,444,699 B2 | 11/2008 | Hense | |
| 7,810,193 B1 | 10/2010 | Ennis | |
| 8,325,934 B2 * | 12/2012 | Kuo | A47G 9/10 |
| | | | 381/71.1 |
| 2007/0061976 A1 * | 3/2007 | Bazargani | A47G 9/1027 |
| | | | 5/644 |
| 2010/0313359 A1 * | 12/2010 | Scott | A47G 9/1027 |
| | | | 5/655.3 |
| 2015/0007393 A1 * | 1/2015 | Palashewski | A47C 27/082 |
| | | | 5/713 |
| 2016/0015184 A1 * | 1/2016 | Nunn | A47C 27/082 |
| | | | 700/282 |
| 2016/0066716 A1 * | 3/2016 | Rao | A61B 5/6814 |
| | | | 600/26 |
| 2017/0215608 A1 * | 8/2017 | Moss | A63H 3/28 |

FOREIGN PATENT DOCUMENTS

| | | | | |
|---|---|---|---|---|
| CN | 106691049 A | | 5/2017 | |
| DE | 602004008045 T2 * | | 4/2008 | A47C 27/082 |
| EP | 1679021 A2 * | | 7/2006 | A47G 9/1027 |

* cited by examiner

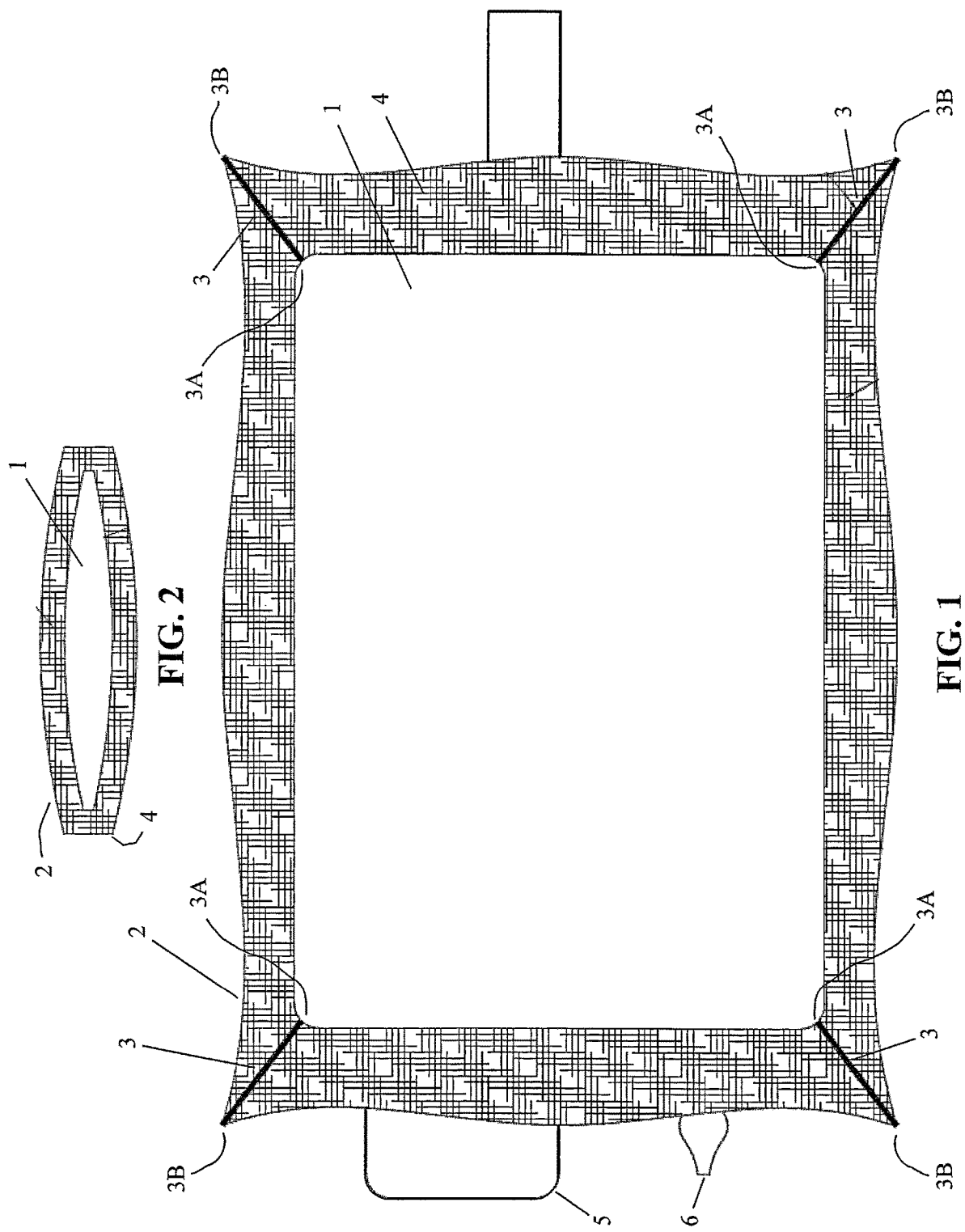

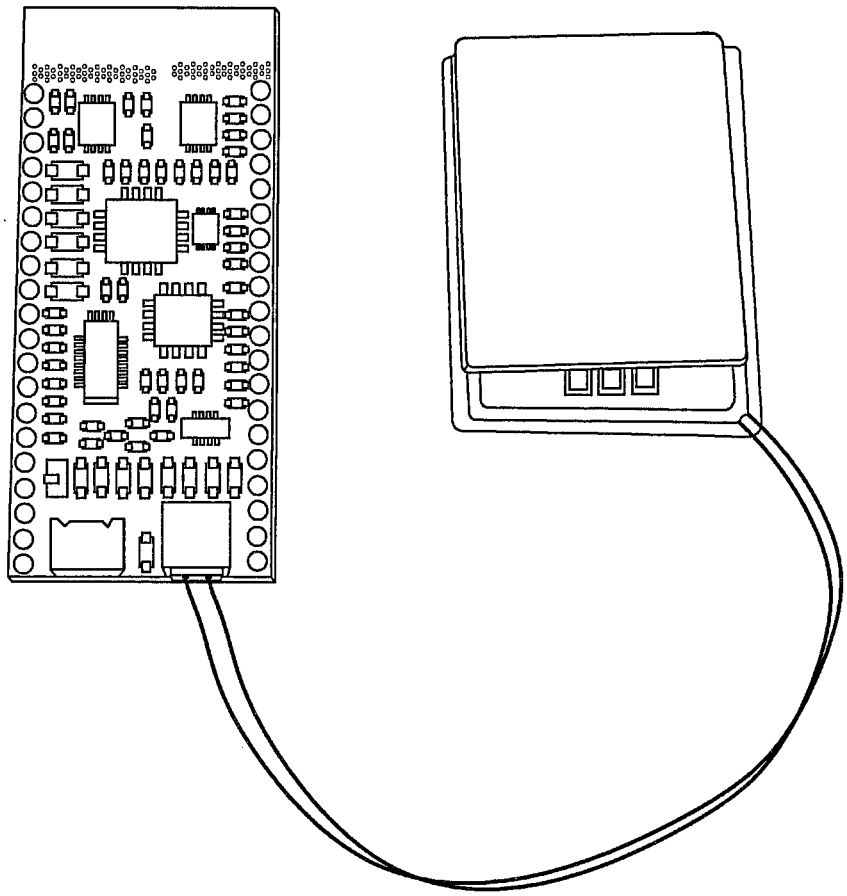

FIG.9
WIFI
Bluetooth
4MBFlash
Lithium battery interface, 500mA Max charging current
Dual-core tensilica LX6 microprocessor
Up to 240MHz clock frequency
520kB internal SRAM
Integrated dual-mode Bluetooth (classic and BLE)
2.2 v OPERATING RANGE
2.5μA DEEP Sleep current
28GPIO
10-electrode capacitive touch support
Hardware accelerated encryption (AES. SHA2, ECC, RSA-4096)
Integrated LiPo Battery

ADJUSTABLE COMFORT PILLOW

CROSS REFERENCES TO RELATED APPLICATIONS

This application is a continuation in part of U.S. application Ser. No. 16/254,790, filed on Jan. 23, 2019, which claims priority on U.S. Provisional Application Ser. No. 62/621,733, filed on Jan. 25, 2018, and this application also claims priority on U.S. Provisional Application Ser. No. 62/884,263, filed on Aug. 8, 2019, and on U.S. Provisional Application Ser. No. 62/898,606, filed on Sep. 11, 2019, all disclosures of which are incorporated herein by reference.

FIELD OF THE INVENTION

The present invention relates to an adjustable comfort pillow that includes an inflatable air bladder positioned inside of a casing and in fluid communication with an air pump to inflate the bladder. The air bladder is also in fluid communication with an air release nozzle to deflate the bladder to a desired air support setting.

BACKGROUND OF THE INVENTION

Providing proper support to different areas of the body, such as the back, neck and spaces between the legs of a person, has always been a point of emphasis by medical practitioners. The vast majority of working adults remain in a stationery sitting position for most if not all of their work day and do not properly support their back and/or neck, which, over a period of time, can lead to the development of chronic back and neck issues. In addition, many people rest or sleep on their sides because it is a very comfortable position. However, while it can be very comfortable, it is no secret that it can lead to the bending of the spinal cord which can lead to unwanted strain on the muscles, ligaments, tendons, bones, and/or joints.

Devices/methods that may be related, and which are not admitted herein to be prior art to the disclosed apparatus, may be shown by the following U.S. Patents and Patent Application Publications: U.S. Pat. No. 2,682,918 to Porter; U.S. Pat. No. 2,691,179 to Kann; U.S. Pat. No. 3,298,044 to Saltness; U.S. Pat. No. 3,303,518 to Ingram; U.S. Pat. No. 3,568,227 to Dunham; U.S. Pat. No. 3,644,949 to Diamond; U.S. Pat. No. 4,389,742 to DeWitt; U.S. Pat. No. 5,708,999 to Priolo; U.S. Pat. No. 5,771,514 to Wilhoit; U.S. Pat. No. 6,510,573 to Grabe; U.S. Pat. No. 6,622,326 to Richardson; U.S. Pat. No. 6,934,989 to Ledvine; U.S. Pat. No. 6,951,038 to Ganoe; U.S. Pat. No. 7,146,665 to Moorin; U.S. Pat. No. 7,444,697 to Williams; U.S. Pat. No. 7,444,699 to Hense; U.S. Pat. No. 7,810,193 to Ennis; U.S. Pat. No. 8,015,972 to Pirzada; and U.S. Pat. No. 8,649,907 to Ersavas; and Chinese Patent No: CN106691049A.

However, there remains a need in the art for a support that is adjustable to a desired size and firmness to provide a user with a desired amount of support and/or comfort. The present invention addresses this need.

OBJECTS OF THE INVENTION

It is an object of the present invention to provide an adjustable pillow that can be inflated to a desired size and firmness to provide desired support and comfort to a user.

It is another object of the present invention to provide an adjustable pillow that is easy and convenient to inflate and deflate.

It is yet another object of the invention to provide an adjustable pillow the size and firmness of which may be adjusted using an application on a smart phone.

It is an even further object of the present invention to provide an adjustable pillow that can be used for therapeutic purposes.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment, a pillow may be adjustable in size and firmness by having an inflatable bladder housed within a casing, such as a pillow case. The adjustable pillow further includes one or more bladder support members that retain the pillow in a central location in the casing. An air pump and air release nozzle are in fluid communication with the bladder to inflate and deflate the bladder, respectively. The air pump and air nozzle may extend out of an opening in a side of the bladder casing for easy access by a user. In addition, pillow stuffing may surround the air bladder inside of the bladder casing to provide a comfortable resting surface for a user. In operation, a user may use the air pump to inflate the bladder to a desired setting. If a user wishes to further adjust the air support provided by the air bladder, a user may further inflate or deflate the air bladder.

BRIEF DESCRIPTION OF THE DRAWINGS

The description of the various example embodiments is explained in conjunction with appended drawings, in which:

FIG. 1 is a top view of the adjustable comfort pillow of the present invention that shows the interior of the pillow casing;

FIG. 2 shows a cross-sectional view of the adjustable comfort pillow of FIG. 1;

FIG. 9 illustrates circuitry and a battery coupled thereto, along with features/specifications of the components/arrangement;

DETAILED DESCRIPTION OF THE INVENTION

Figure 3A:
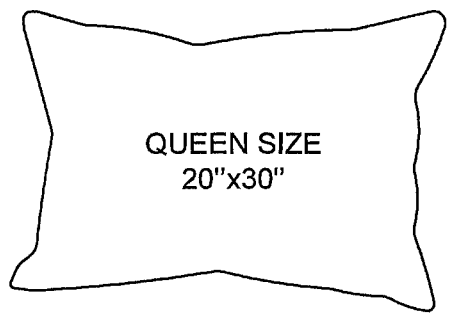
FIG. 3A shows a representative size for one embodiment of a pillow formed in accordance with the present invention.
Figure 3B:
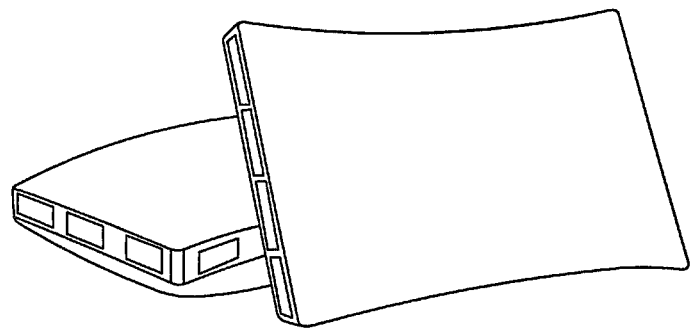
FIG. 3B illustrates a style of one embodiment of a pillow formed in accordance with the present invention.
Figure 3C:
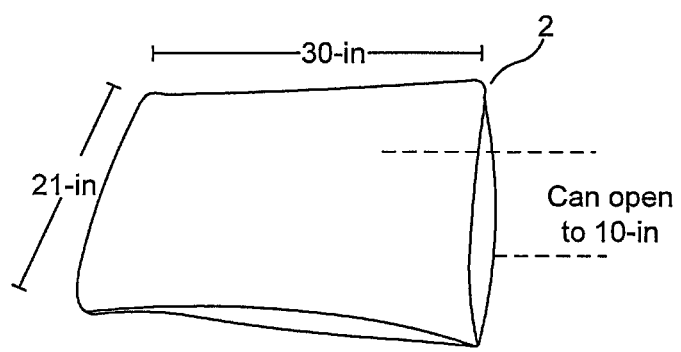
FIG. 3C illustrates certain dimensions for one embodiment of a pillow formed in accordance with the present invention.
Figure 4:
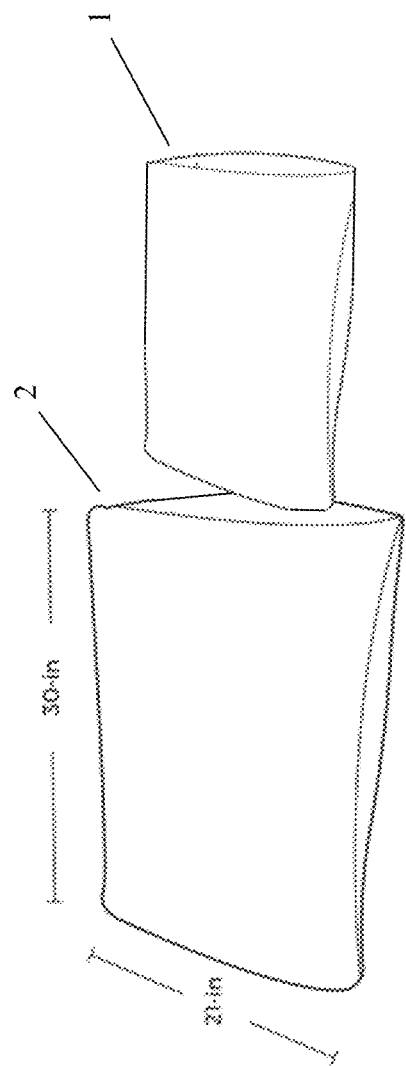
FIG. 4 illustrates one embodiment of a pillow formed in accordance with the present invention, having an inner portion and an outer portion.
Figure 5:
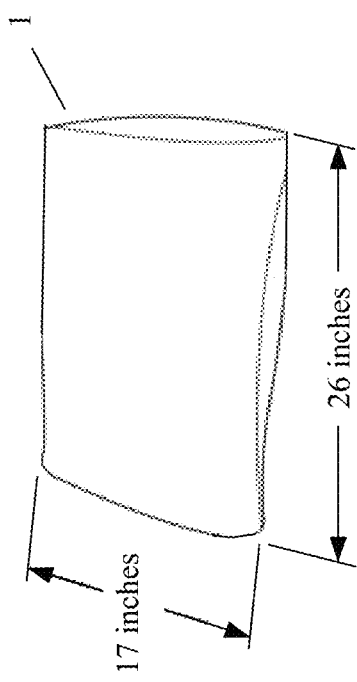
FIG. 5 illustrates exemplary dimensions for the inner pillow portion shown in FIG. 4.
Figure 6:
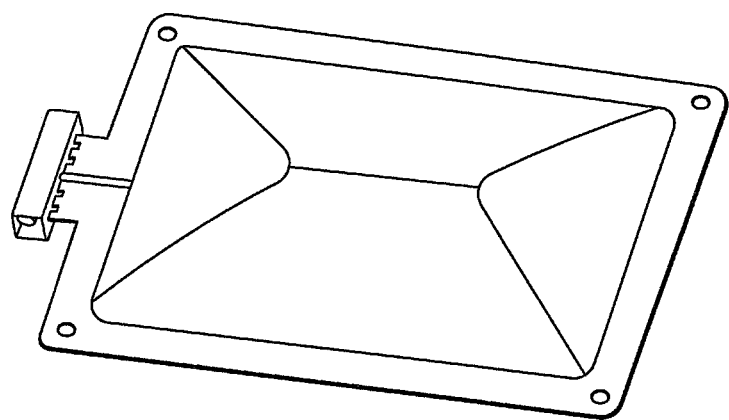
FIG. 6 illustrates another embodiment of a pillow formed in accordance with the present invention having an external battery pack.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit (e.g., for a 0.1250 inch shaft diameter the opening may be 0.1285 inches for a close fit and may be 0.1360 inches for a free (running) fit; and for a 0.5000 inch diameter shaft size the opening may be 0.5156 inches for a close clearance fit and may be 0.5312 inches for a free clearance fit). Other clearance amounts may also be used.

FIG. 1 details a top view of one embodiment of the present invention that shows the components located in the interior of the casing. It shows the adjustable pillow as including an inflatable air bladder 1 that is housed within a casing 2. The bladder 1 and casing 2 may each have a substantially rectangular shape, and the casing may be formed in such a manner to centrally position the bladder therein. In one embodiment the casing may be secured together at each corner by support members 3 to suitably position the bladder therein. The support members 3 are elongate members that are secured to a corner of the interior surface of the bladder casing 2 at one end 3a of the support members 3 and secured to a corner of the exterior surface of the inflatable bladder 1 at an opposite end 3b of the support members. The support members keep the bladder 1 centered within the casing 2. Other structural arrangements for securing the air bladder 1 within the casing 2 may also be used. The casing 2 may be a flexible cloth, such as that which is regularly used for a pillow case and is capable of expanding as the bladder therein expands. As is shown in FIG. 1, the casing is larger than the bladder such that there is a space between the casing and the bladder. In this space, pillow stuffing 4 may be inserted. The stuffing may include, but is not limited to, feathers and/or conventional foam and/or memory foam and/or microfibers and/or other pillow stuffing materials known in the art. The stuffing 4 should be thick enough so that the person using the pillow does not feel the inner bladder 1, from the top, bottom, or sides. The stuffing provides a comfortable resting surface for a user, such as a person or pet.

Also shown in FIG. 1 is an air pump 5 may be in fluid communication with the inflatable bladder 1 via tubes, etc. In various embodiments the air pump 5 that allows a user to selectively inflate the bladder may be a rubber squeeze type (see e.g., U.S. Pat. No. 795,108 to Doellinger; U.S. Pat. No. 3,411,164 to Sumergrade; U.S. Pat. No. 3,633,567 to Sarnoff; and U.S. Pat. No. 5,628,721 to Arnold); or may be a motorized type of hand pump, including, but not limited to a 3 volt pump motor. In another embodiment an inflation valve may be in communication with the bladder and may have removable cap, which valve may accommodate a user blowing into the valve hole or a manual pump or a compressor that supplies air therein. Examples of such valves include, but are not limited to, the following U.S. Pat. No. 2,977,972 to Chakine; U.S. Pat. No. 5,351,711 to Peter; U.S. Pat. No. 5,358,001 to Smith; and U.S. Pat. No. 6,164,314 to Saputo. A separate nozzle/valve 6 for releasing air from the bladder may also be in fluid communication with the inflatable bladder 1. The nozzle 6 is preferably a rubber squeeze type nozzle that allows a user to selectively deflate the bladder but it may be any other nozzle that is known by those of ordinary skill in the art. The air pump 5 may extend out of one opening (not shown) and the nozzle 6 may extend out of a second opening (not shown) in the bladder casing 2 so that they are accessible without having to reach inside of the casing, but other configurations are possible, such as the air pump and nozzle extending out of the same opening. The openings that the pump and nozzle extend from are also preferably sealed around the edges of the pump and nozzle to prevent any of the components stored inside of the casing from falling out, such as the stuffing stored therein.

FIG. 2 shows a vertical cross-sectional view of the adjustable pillow of FIG. 1. It shows the inflatable bladder 1 as being positioned within the bladder casing 2 and having stuffing 4 in the spaces between the exterior surface of the bladder 1 and the interior surface of the casing 2. Note that the dimensions shown in the figures are exemplary, and in general are not meant to limit the size of the pillow that may be constructed.

The present invention allows a user to adjust the height and firmness of a pillow and may be used in the house, outdoors, during travel, etc. When the bladder is not inflated, the support from the pillow is only provided by the stuffing that is present in the pillow casing. When the bladder is inflated to a desired air and firmness level, a desired support will be provided by the bladder. For example, a user can inflate the bladder to around its maximum air-containing capacity such that the bladder will not lose its shape when a force is applied thereto because there will be little room in the interior of the bladder for air to be displaced. This setting will provide a user with high amount of support and firmness.

On the other hand, a user can inflate the bladder to a lesser capacity such that there is room in the bladder for air to be displaced when a force is applied to the bladder. For example, a person may rest his or her head on the bladder and the bladder conform to the shape of the person's head by air being displaced within the bladder in response to the force being applied thereto.

The bladder is preferably made of rubber but it may be made of any other material that is flexible yet durable so that it can withstand the rigors associated with being used to provide support. The air pump and nozzle are also preferably rubber but in other embodiments they may also be made of any alternative material that is flexible but durable.

The one or more support members are preferably made of a material that is strong enough to maintain the bladder in a substantially fixed position within the casing but that also have an elastic character so that the support members are not easily broken or otherwise damaged when a force is applied thereto. In addition, the support members may also be placed in different locations rather than or in addition to the corners of the bladder and pillow casing. These locations may include one or more support members being secured at any point along any of the one or more sides of the pillow casing and bladder. An example of a point is at the midpoint of each side of the pillow casing and bladder. Placing additional securing members may help in further restraining movement of the bladder within the pillow casing. The support members are preferably non-removably attached to the bladder and/or casing by sewing or other attachment means used by those of ordinary skill in the relevant art, but they may be removably attached in other embodiments.

The casing may also include an opening along its surface in addition to the openings that receive the pump and nozzle. In one embodiment the opening is preferably sealable by a zipper, etc. and will allow a person to reach the contents stored inside of the casing when unzipped.

In addition to being used as a resting aid, the adjustable pillow may also be used therapeutically to provide therapeutic support and comfort to different areas of the body. In one use, the pillow can be placed behind a user's neck to provide the desired support and comfort. In another use, the pillow can be placed behind a user's back. In an even further use, the pillow can be placed between the calves, knees, and/or thighs of a user. Additional therapeutic uses not described herein but that involve providing support and/or comfort to one or more areas of the body are also possible.

An even further use of the adjustable pillow is to occupy spaces for the storage and/or movement of items to prevent any damage or destruction that may otherwise occur if no cushion or support was provided. In this embodiment, the adjustable pillow may be positioned in one or more voids that may be present in a storage area. For example, a person loading the trunk of a car may place the adjustable pillow in spaces that are present between items in the trunk. The person may then inflate the bladder to a desired size so that a desired amount of space is occupied and cushion and support provided.

In an even further embodiment of the present invention, the bladder may be configured to receive a liquid fluid rather than or in addition a gaseous fluid. In this embodiment, the bladder may be designed to have at least one gas receiving compartment and/or at least one liquid receiving compartment. A means for providing liquid to and removing liquid from the compartment may also be provided in this embodiment. An embodiment having one gas containing compartment and one liquid containing compartment gives a user the choice of which compartment to use since both compartments will have different properties and provide different types of support and/or comfort.

Figure 7A:
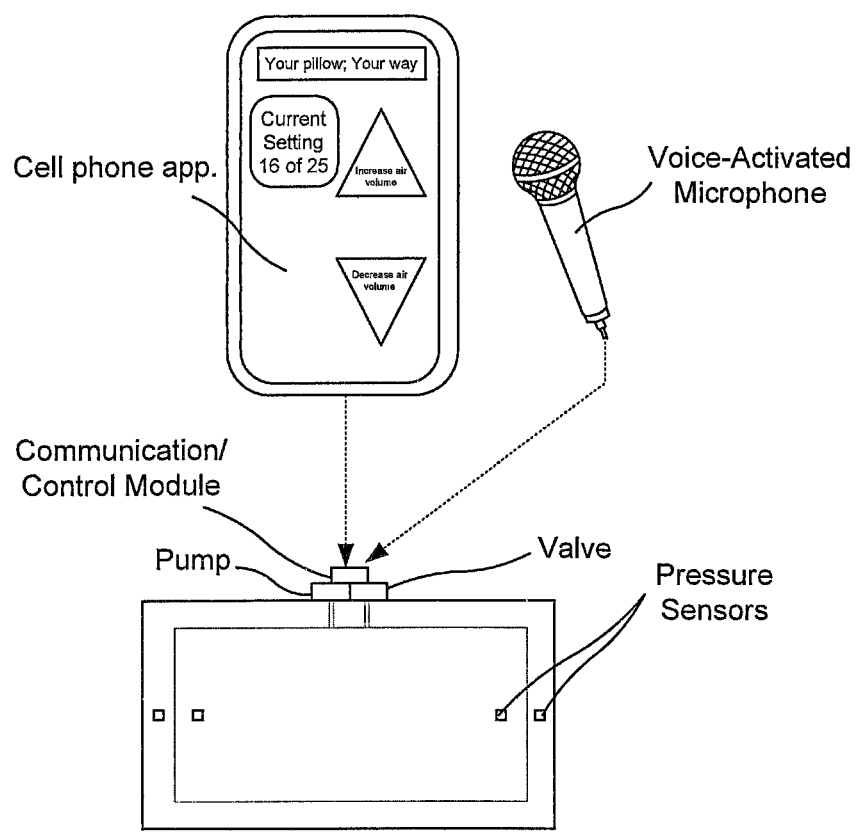
FIG. 7A illustrates a touchscreen of a mobile computing device (e.g., a cell phone) that is running an application that is coupled wirelessly to at least a portion of the circuitry of the pillow of the present invention, and which computing device displays a graphic user interface (GUI) that includes control buttons that may be used to control/alter the inflation/settings for the pillow.
Figure 7B:
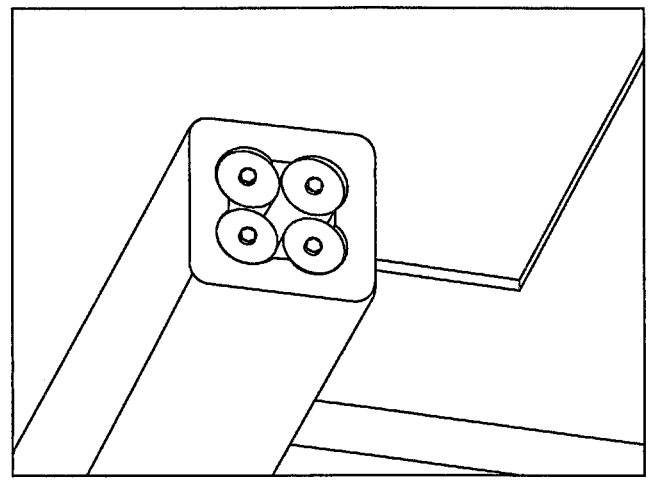
FIG. 7B illustrates an end view of the battery pack shown in FIG. 6.

As seen at least in FIGS. 7A, 9, and 10A-11D, another embodiment of the adjustable comfort pillow may also include electronics with at least one cellular communication module configured to remotely control a pump and a valve to adjust the firmness of the pillow by causing further inflation and/or deflation of the bladder therein, which control may be directed by a person using an application running on a mobile electronic device (e.g., a smart phone), which may be done using a Bluetooth connection, and with the person using a Bluetooth car bud, etc. As seen in FIG. 7A, the software application running on the user's smart phone may permit incremental adjustments to the inflation level (firmer/softer) using buttons on a graphical user interface displayed on the touch screen of the device.

In another embodiment, a voice activate microphone and switch may be configured to transmit voice commands to a processor to audibly control (activate/deactivate) the pump and valve to control the inflation level, so that the user may make changes to the inflation level without having to manually toggle the controls button(s) on the pillow or on the GUI of the cell phone screen. The microphone may be wired to the communication/control module that activates the pump and/or the valve, or alternatively the microphone may communicate wirelessly with the communication/control module and could be located distally from the pillow (e.g., on the bed's headboard). The capability to audibly control the pillow's level of inflation is especially convenient for making adjustments to the inflation level even in the middle of the night, particularly when a user may be having difficulty finding a comfortable position for a restful sleep.

In addition, although most people typically sleep predominantly on either their side or their back (i.e., are a back-sleeper or a side sleeper), they often will nonetheless change between those two positions one or more times during the course of a single night's sleep, which would ideally require a corresponding adjustment to the level of inflation (e.g., greater inflation for side sleeping and less inflation for back-sleeping). Therefore, the communication/control module, in addition to having a numeric scale for the level of inflation (see FIG. 7A—"Current Setting 16 of 25"), may also accommodate a plurality of preset inflation levels that may be defined by the user. Therefore the user may audibly command that the inflation level of 16 be a "side setting" and that an inflation level of 10 be a "back setting" (i.e., a lower inflation level), such that the user may audibly switch between the "side setting" and "back setting" during the course of a night depending upon his/her position.

In yet another embodiment, one or more pressure sensors may be positioned on each of the lateral disposed sides of the pillow to determine when the sleeper has rolled to either his/her left side or the right side, and is in a side sleeping position, which may automatically trigger a change in the inflation level to the preferred side sleeping inflation level from the preferred back-sleeping inflation level, and vice versa.

Figure 7C:
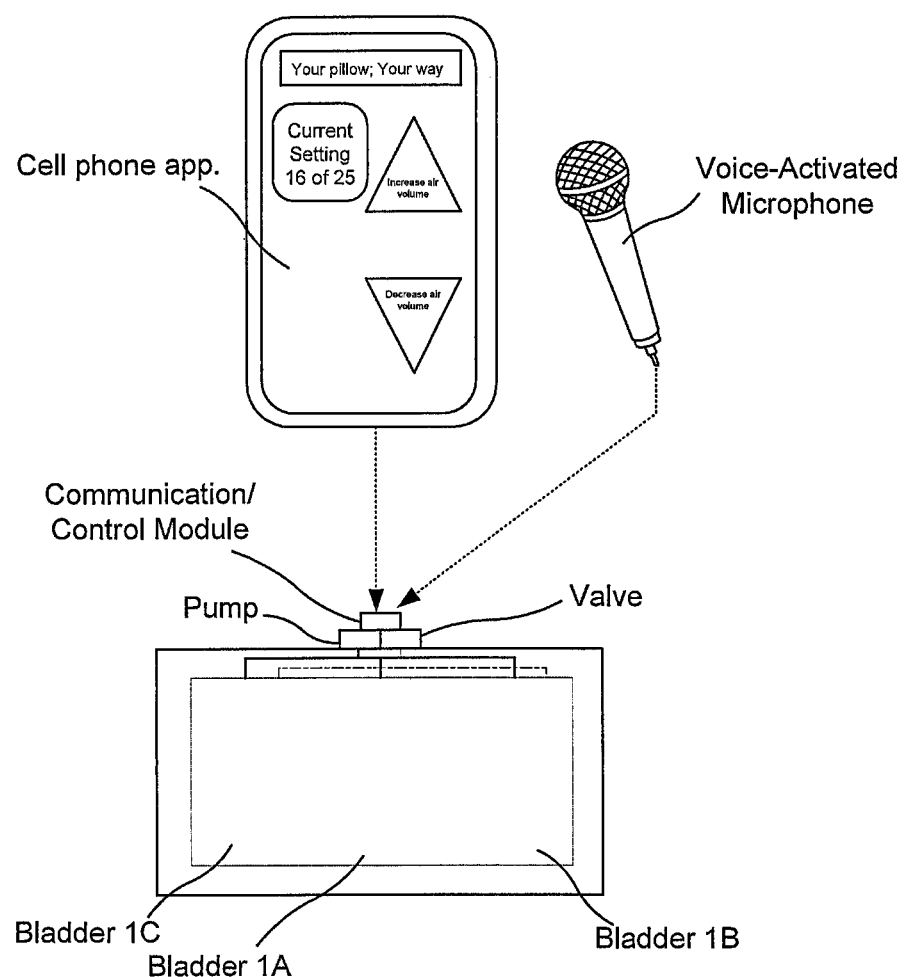
FIG. 7C is an alternate embodiment of pillow and control arrangement shown in FIG. 7A.
Figure 8:
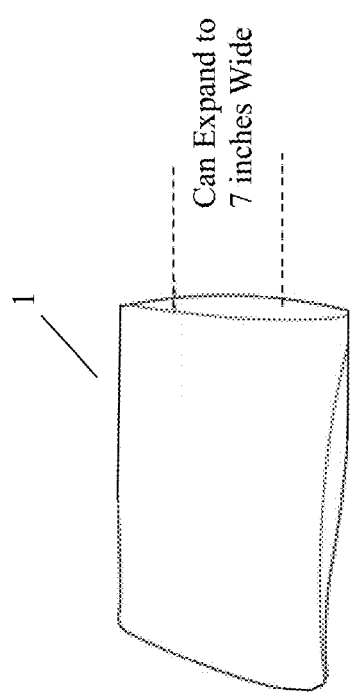
FIG. 8 illustrates options for an inner pillow portion formed in accordance with at least one embodiment of the present invention.
Figure 10A:
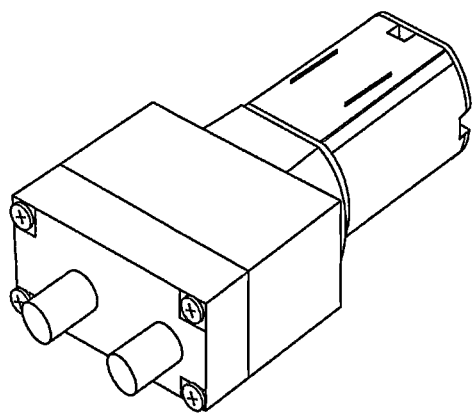
FIG. 10A illustrates a first view of a connector used with at least one embodiment of the present invention.
Figure 10B:
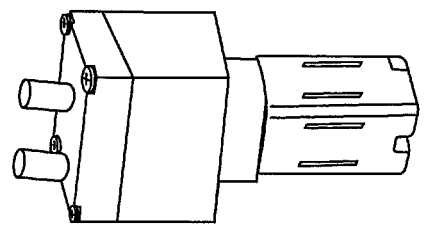
FIG. 10B illustrates a second view of the connector of FIG. 10A.
Figure 10C:
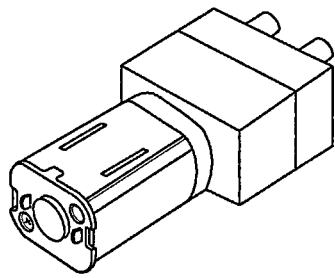
FIG. 10C illustrates a third view of the connector of FIG. 10A.
Figure 10E:
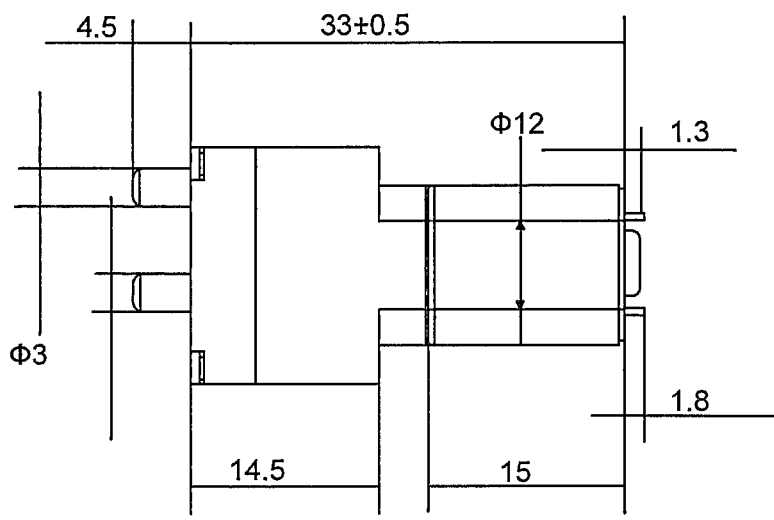
FIG. 10E illustrates a fifth view of the connector of FIG. 10A.
Figure 10F:
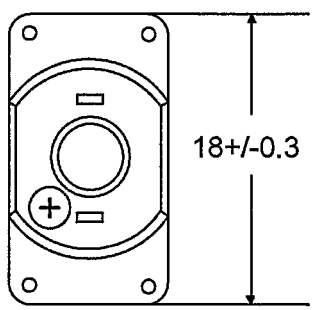
FIG. 10F illustrates a sixth view of the connector of FIG. 10A.
Figure 10D:
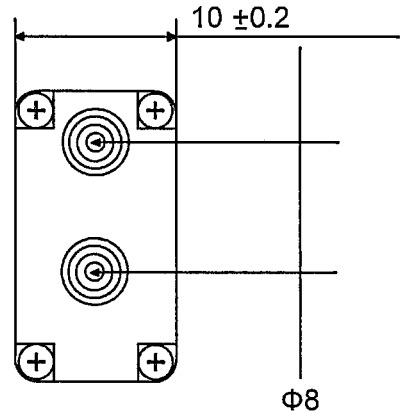
FIG. 10D illustrates a fourth view of the connector of FIG. 10A.
Figure 11A:
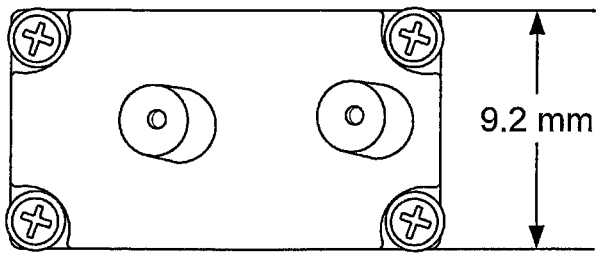
FIG. 11A illustrates a seventh view of the connector of FIG. 10A.
Figure 11B:
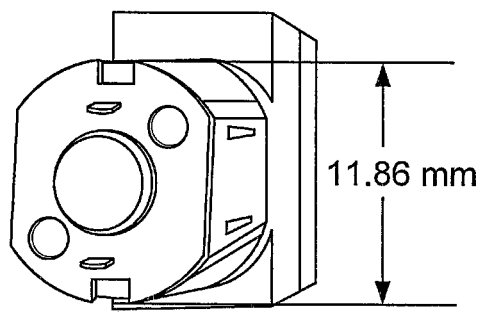
FIG. 11B illustrates an eighth view of the connector of FIG. 10A.
Figure 11C:
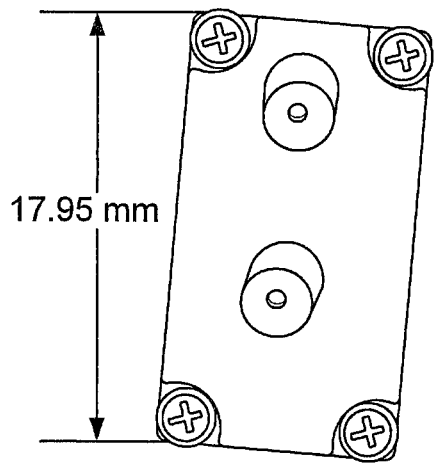
FIG. 11C illustrates a ninth view of the connector of FIG. 10A.
Figure 11D:
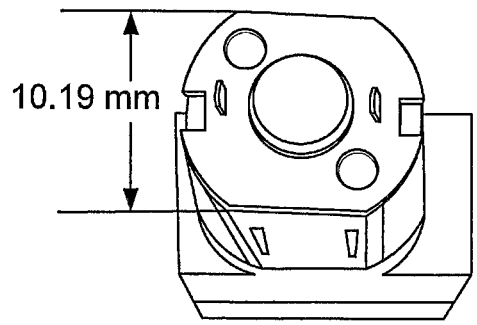
FIG. 11D illustrates a tenth view of the connector of FIG. 10A.
Figure 12:
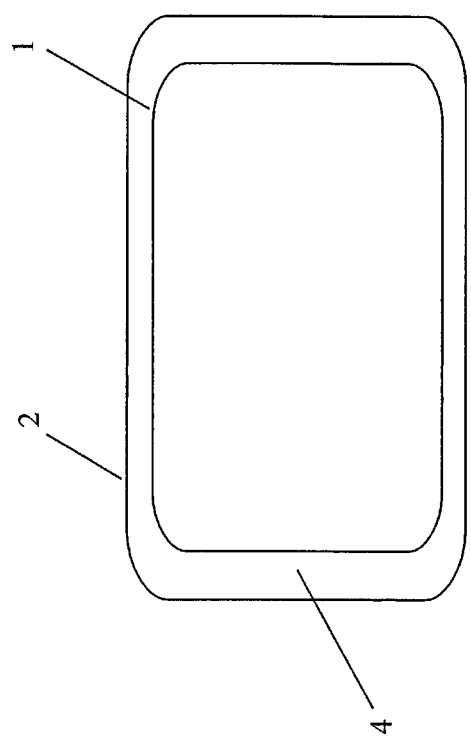
FIG. 12 illustrates the inner pillow inside of the outer pillow, with an enlarged detail view showing inner stuffing of the outer pillow being memory foam.

In yet a further embodiment that is shown in FIG. 7C, a disclosed pillow may have three separate bladders, a first bladder 1A being centrally positioned, and two laterally positioned bladders 1B and 1C along the length of the rectangular pillow, each of which may be separately inflated and deflated by the pump and valve to a desired inflation level by the user, to customize the inflation level for the sleeper's preferred back sleeping position, and each of the sleeper's right side and left side preferred sleeping positions. In one embodiment bladders 1B and 1C may generally be the same size as bladder 1A, and in another embodiment bladders 1B and 1C are preferably each larger (e.g., deeper) than bladder 1A, being preferably between 10 percent to 60 percent larger, or more preferably being preferably between 20 percent to 50 percent larger, and most preferably being between 30 percent to 40 percent larger.

Figure 13:
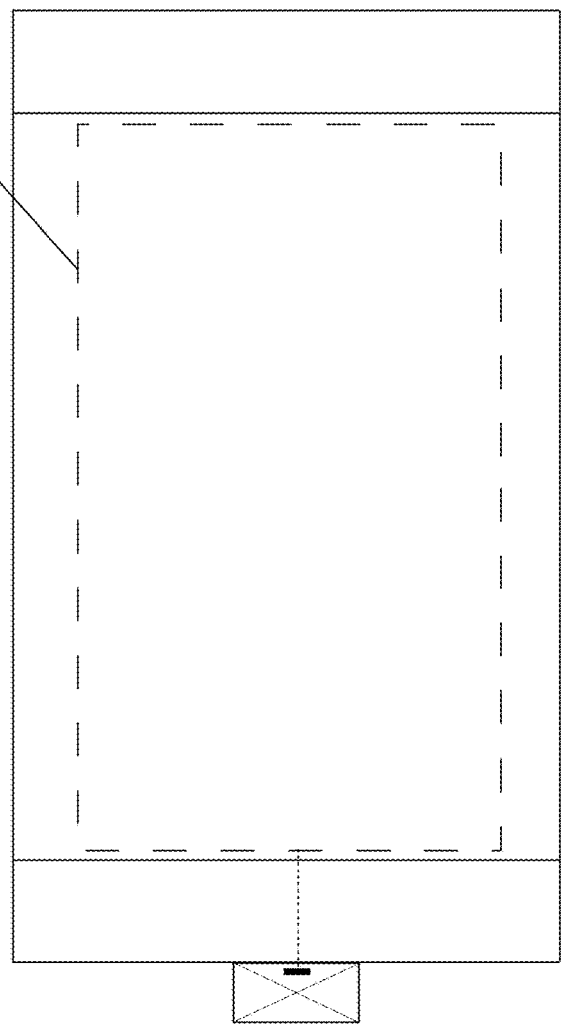
FIG. 13 is a top view of another embodiment of an adjustable pillow formed in accordance with the present invention, having a plurality of individually inflatable/deflatable bladders surrounded by memory foam.
Figure 14:
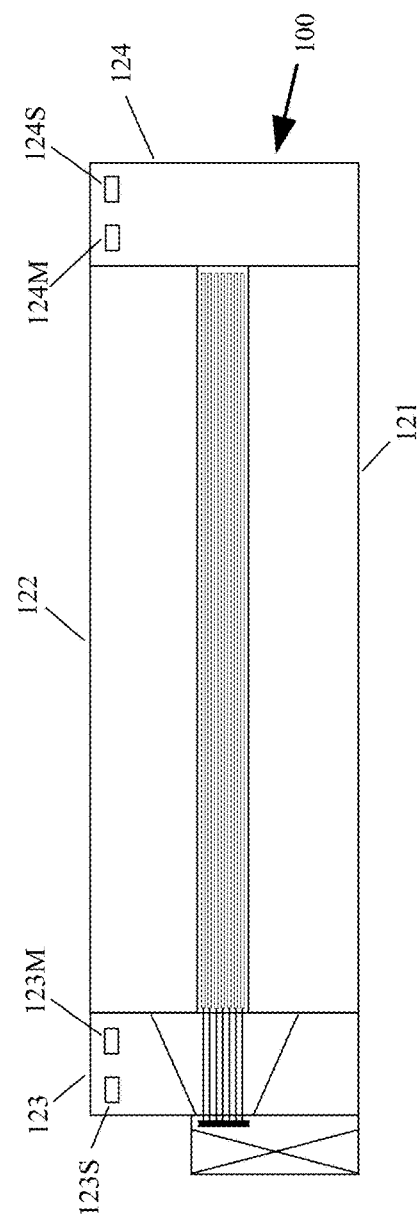
FIG. 14 is a side view of the adjustable pillow of FIG. 13, shown with the bladders in a deflated condition.
Figure 15:
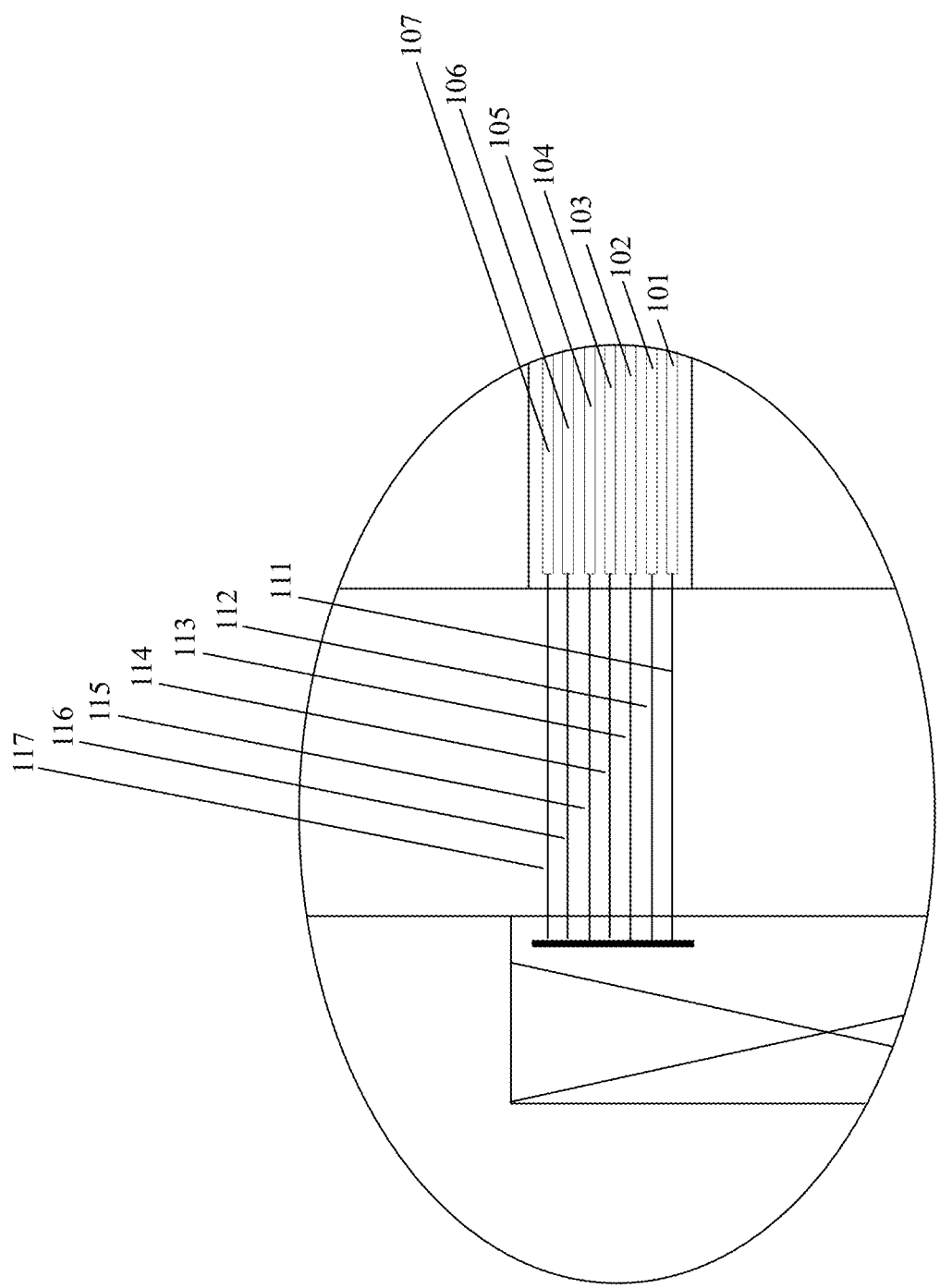
FIG. 15 is an enlarged detail view of the tubes coupled between the pump and the individually inflatable bladders shown in FIG. 13.

In another embodiment shown in FIG. 13 and FIG. 14, the pillow 100 may be formed with a lower layer of foam 121, and an upper layer of foam 122, being separated by a plurality of individually inflatable bladders each having substantially the same size and shape, (e.g., seven bladders—101, 102, 103, 104, 105, 106, and 107), and a first end cap of foam 123 and a second end cap of foam 124, which form a cavity in the foam so the foam encapsulates the bladders. In one embodiment the foam for any or all of the lower layer 121, the upper layer 122, the first end cap 123, and the second end cap 124 may be a memory foam. In another embodiment the foam may be a high expansion foam. In one embodiment the lower layer 121, the upper layer 122, the first end cap 123, and the second end cap 124 may be formed as a single integral piece of foam, with an opening into a cavity that houses the plurality of individually inflatable bladders. In another embodiment, the lower layer 121, the upper layer 122, the first end cap 123, and the second end cap 124 are formed as individual pieces of foam, and are joined together in any suitable manner, including, but not limited to, adhesive bonding. In yet another embodiment, only two pieces of foam may be used, and may be formed to encapsulate the plurality of individually inflatable bladders, being a first piece of foam that may have a properly sized and shaped recess formed therein to receive the bladders, and a second piece of foam that may cover the bladders, and is joined to the first piece of foam.

Each of the individually inflatable bladders may be coupled to a respective tube (e.g., tubes 111, 112, 113, 114, 115, 116, and 117), which may be coupled to a pump configured to inflate each bladder individually as required by an inflation volume set by the user on the application (i.e., only bladder 101; or only bladders 101 and 102; or only bladders 101, 102, and 103; etc.). Apparatus within the pillow (e.g., sensors and corresponding electronics, and gauges) may periodically (e.g., every 12-24 hours) measure the inflation pressure and/or volume, and adjust the measured amount to match the preset chosen by the user.

The use of the adjustable pillow in combination with the application running on a cell phone permits a doctor or medical technician to also remotely monitor the inflation level and adjust it, particularly for a patient who is suffering from cervical injuries.

Figure 16:
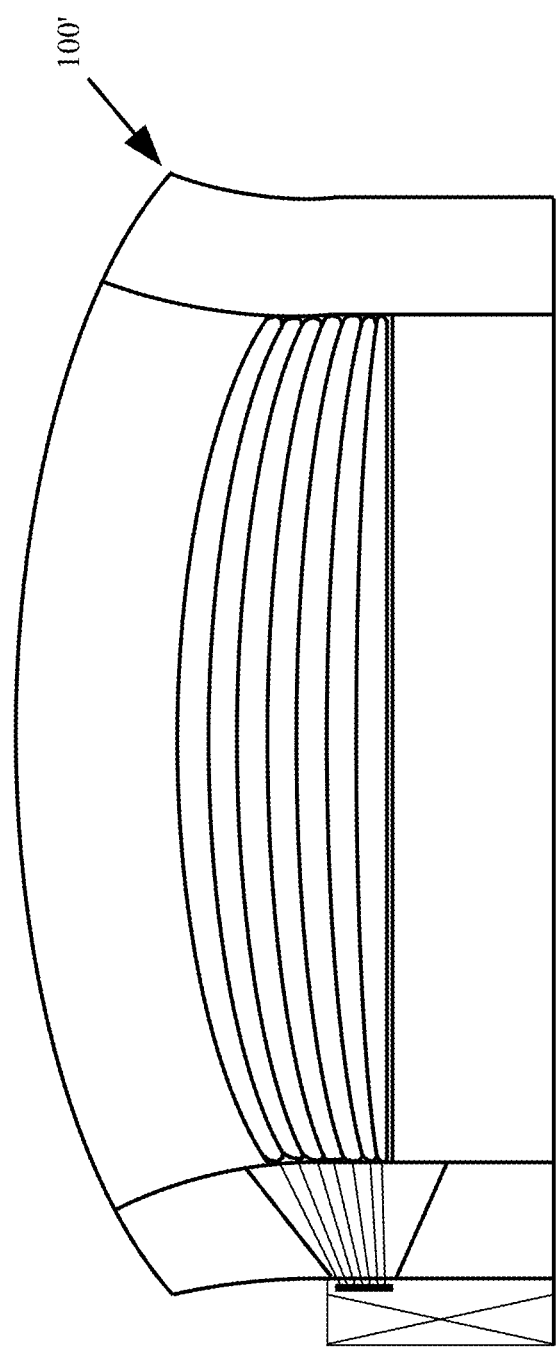
FIG. 16 is the adjustable pillow of FIG. 13 shown with the bladders inflated.

In one embodiment of pillow 100, there may be 3.5 inch layers 121/122 of memory foam, and sufficient bladder capability to increase at least a portion of the pillow height from substantially the 7 inch memory foam height to about a 17 inches height, as shown by pillow 100' in FIG. 16.

In another embodiment of pillow 100, there may be a first speaker 123S and/or a second speaker 124S, which may be positioned within the ends caps 123 and 124, respectively. The speakers 123S/124S may be wired, or more preferably may be wireless speakers, and may be configured to project sound from signals received from a wired or wireless connection with a television, or radio, or any other source. In another embodiment, a radio itself may be incorporated in the pillow.

In yet another embodiment, the pillow 100 may include one or more voice activated microphones (e.g., voice activated microphones 123M/124M) that may be configured as described hereinabove, and may be further configured in combination with electronic circuitry that includes but is not limited to a processor, to receive and detect snoring sounds made by the sleeper, and to actuate one or more valves or actuate the pump to deflate or further inflate the pillow to make height adjustments (down or up) to eliminate or reduce the snoring being experienced by the sleeper. The height adjustments may be made immediately upon detection of the snoring, or may instead be made after the snoring reaches a threshold loudness, or upon exceeding a threshold duration. In addition, in another embodiment the one or more voice activated microphones may more broadly be configured to respond to a "wake" word and a verbal request, which microphone(s) may be coupled to a networked system that may include, for example, an audio system, such that the verbal utterance may cause the audio system to play music according to the verbal command. Other voice assistant services may also be provided by the one or more voice activated microphones (see e.g., U.S. Pat. No. 6,711,543 to Cameron; U.S. Pat. No. 8,068,881 to Schrager; U.S. Pat. No. 8,112,037 to Ketari; U.S. Pat. No. 8,255,225 to Byford; and U.S. Pat. No. 9,659,577 to Langhammer).

In yet another embodiment, a pillow case may be formed of a material (e.g., an elastic material) that can adjust to the height changes experienced by the pillow 100, without losing its shape. The pillow case may also have openings that may be aligned with openings in the pillow itself, and/or aligned with equipment housed therein that may require attachment of power cords for recharging, or may be aligned with any other type(s) of features of the pillow.

Figure 17:
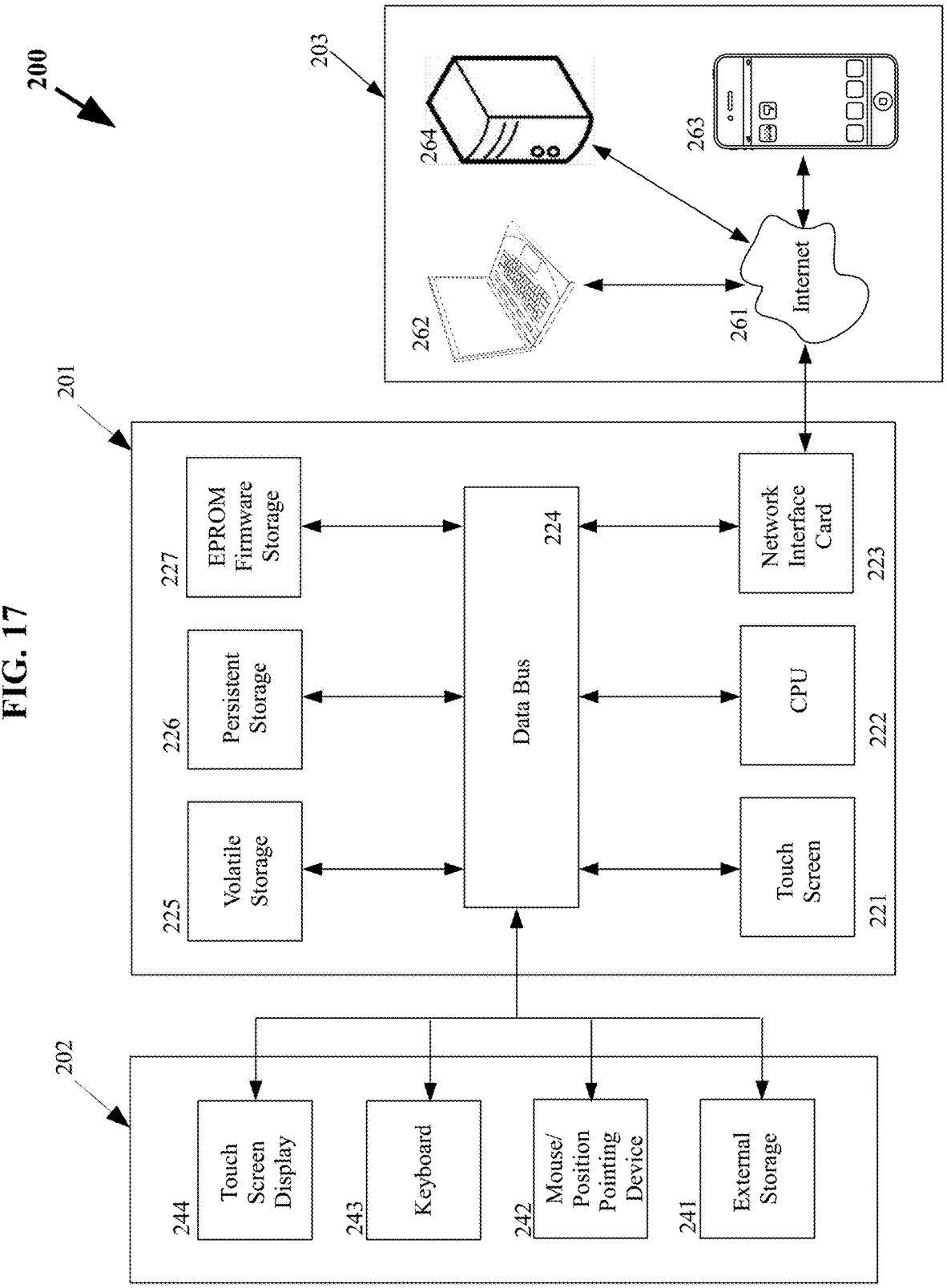
FIG. 17 is a schematic illustration showing an exemplary computing unit capable of being programmed by the instructions of the software of the present invention, and which may include personal computers, cellular phones, and other mobile computing devices.

Software of the present invention may run on a suitable computing device, such as a server, a tablet, a cell phone, or other mobile smart device, so a description of such an accessorized exemplary computer system is hereinafter disclosed, even though a particular embodiment may not require all of the described components. Exemplary computer system 200 (i.e., a client device associated with a particular user) is shown schematically in FIG. 17, and which may comprise computing unit 201 interacting with external peripherals 202, such as a separate touch screen display 244, and interacting with network resources 203, including use of the internet 261, and other computers (or other client devices or a server), which may be a laptop computer 262 (i.e., a second client device associated with a second user), a smart phone 263 (i.e., a third client device associated with a third user), a server 264, etc.

The computing unit 201 may include a data bus 224 for communicating information across and among various parts of computing unit 201, and a central processing unit, which may be a microprocessor (hereinafter "processor" or "CPU") 222 coupled with a bus 224 for processing information and performing other computational and control tasks. Computing unit 201 may also include a volatile storage 225, such as a random access memory (RAM) or other dynamic storage device, coupled to bus 224 for storing various information as well as instructions to be executed by processor 222. The volatile storage 225 may also be used for storing temporary variables or other intermediate information during execution of instructions by processor 222. Computing unit 201 may further include a read only memory (ROM) or an erasable programmable memory (EPROM) 227 or other static non-transitory storage device coupled to bus 224 for storing static information and instructions for processor 222, such as basic input-output system (BIOS), as well as various system configuration parameters. A persistent storage device or non-volatile memory 226, such as a magnetic disk, optical disk, or solid-state flash memory device may be provided and may be coupled to bus 224 for storing information and instructions.

Computing unit 201 may be coupled via bus 224 to an integral display 221, possibly a touch-screen display, for use in displaying information to a user. If desired, computing unit 201 may be coupled via bus 224 to an external display screen 244. An external input device 243 (e.g., a standard keyboard) may be coupled to bus 224 for communicating information and command selections to processor 222. A cursor control device 242, such as a mouse, a trackball, or cursor direction keys, may be used for communicating direction information and command selections to processor 222 and for controlling cursor movement on display 244. An external storage device 241 may be connected to the computing unit 201 via bus 224 to provide an extra or removable storage capacity for the computing unit 201, which may be used to facilitate exchange of data with other computer systems.

Some of the techniques herein may be performed by computing unit 201 in response to processor 222 executing one or more sequences of one or more instructions contained in the volatile memory 225. Execution of the sequences of instructions contained in a non-transitory memory may cause processor 222 to perform the process steps described herein. In alternative embodiments, specific hard-wired digital circuitry may be used in place of, or in combination with, software instructions to implement the invention.

The term "computer-readable medium" as used herein refers to any medium that participates in providing instructions to processor 222 for execution. The computer-readable medium is just one example of a machine-readable medium, which may carry instructions for implementing any of the methods and/or techniques described herein. Various forms of computer readable media may contain one or more sequences of one or more instructions for the processor 222 to execute, including non-volatile media (storage device 226), and volatile media (storage device 225). Common forms of non-transitory computer-readable media include, for example, a floppy disk, a hard disk, magnetic tape, or any other magnetic medium, a CD-ROM, a flash drive, and a memory card.

The computing unit 201 may thus also include a communication interface, such as network interface card 223 coupled to the data bus 222. Communication interface 223 may provide a two-way data communication coupling to a network link that may be connected to a local network. For example, communication interface 223 may be an integrated services digital network (ISDN) card or a modem to provide a data communication connection to a corresponding type of telephone line, or it may be a local area network interface card (LAN NIC) to provide a data communication connection to a compatible LAN.

Network link 223 also typically provides data communication to other network resources. For example, the network link may provide a connection over the internet 261 to the world-wide-web. Thus, the computing unit 201 can access resources located anywhere using the Internet 261. Also, the computing unit 201 may also be accessed by, or communicate with, other computers (e.g. 262), or another smart device (e.g., smartphone 263), generally with permission, and which may be located anywhere with access to the internet 261.

While illustrative implementations of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. An adjustable pillow comprising: a lower layer of foam; an upper layer of foam, a first end cap of foam; a second end cap of foam wherein said lower layer of foam, said upper layer of foam, said first end cap of foam, and said second end cap of foam are joined together and form a cavity therein; a plurality of individually inflatable bladders, said plurality of individually inflatable bladders positioned in said cavity; wherein each of said plurality of individually inflatable bladders has a same size and shape; wherein said plurality of individually inflatable bladders are positioned in a stack; a respective tube in fluid communication with each of said plurality of individually inflatable bladders; a pump, said pump configured, when activated, to inflate any one or more of said plurality of individually inflatable bladders to a particular pressure, to increase a height of said adjustable pillow; one or more valves, said one or more valves configured, when activated, to deflate any one or more of said plurality of individually inflatable bladders to decrease a height of said adjustable pillow; a processor and electronic circuitry configured to activate and deactivate said pump to increase the height of said adjustable pillow, and being further configured to activate and deactivate said one or more valves to decrease the height of said adjustable pillow; a communication and control module configured to control said processor to adjust inflation of said plurality of individually inflatable bladders according to a range of numeric settings, each setting corresponding to a different inflation level and corresponding height of said adjustable pillow; one or more voice activated microphones electronically coupled to said processor and electronic circuitry; wherein said communication and control module is further configured to receive a voice command received by said one or more voice activated microphones for selection of any setting from among said range of settings to adjust the inflation level and height of said adjustable pillow according to the selected setting; wherein said communication and control module is further configured to receive a voice command to assign a first setting from among said range of settings to be a side sleep position setting, and to receive a voice command to assign a second setting of said range of settings to be a back sleep position setting; wherein said communication and control module is further configured to receive a voice command of side sleep position to adjust the height of said pillow according to said first setting, and to receive a voice command of back sleep position to adjust the height of said pillow according to said second setting; wherein said communication and control module is further configured to receive data from an application on a mobile communication device, permitting a doctor to remotely monitor said inflation level for a patient with cervical injuries; wherein said communication and control module is further configured to transmit commands from the application on the mobile communication device, to control said pump to change said inflation level; a first speaker and a second speaker respectively positioned within said first and second ends caps of foam, and configured to project sound from signals received from a wired or wireless connection with one or more of: a television, and a radio; wherein said one or more voice activated microphones are configured to respond to a verbal request to turn said sound on or off; wherein said electronic circuitry is configured to turn said projected sound on or off according to the verbal request detected by said one or more voice activated microphones; and wherein said one or more voice activated microphones are configured to receive and detect snoring sounds made by a user, said processor configured to actuate said one or more valves or actuate said pump to correspondingly deflate or further inflate said pillow to make height adjustments until the detected snoring sounds fall below a threshold level.

2. The adjustable pillow of claim 1, wherein said lower layer of foam is about 3.5 inches thick and said upper layer of foam is about 3.5 inches thick; and wherein said plurality of bladders are configured to increase the height of at least a portion of said pillow for a total pillow height of about 17 inches.

3. The adjustable pillow of claim 1, wherein said plurality of individually inflatable bladders comprises at least seven bladders.

4. The adjustable pillow of claim 1, wherein said lower layer of foam, said upper layer of foam, said first end cap of foam, and said second end cap of foam are formed as individual pieces of foam and joined together to form the cavity.

5. The adjustable pillow of claim 1, wherein said lower layer of foam, said upper layer of foam, said first end cap of foam, and said second end cap of foam are integrally formed as a single unitary piece of foam, with a slit into the cavity.

6. The adjustable pillow of claim 1, wherein said foam is foam from the group of foams consisting of: a memory foam; and a high expansion foam.

7. The adjustable pillow of claim 1, further comprising: a second plurality of individually inflatable bladders, said second plurality of individually inflatable bladders positioned in said cavity on a first side of said first plurality of individually inflatable bladders; a third plurality of individually inflatable bladders, said third plurality of individually inflatable bladders positioned in said cavity on a second side of said first plurality of individually inflatable bladders; a first pressure sensor positioned at said second plurality of individually inflatable bladders; a second pressure sensor positioned at said third plurality of individually inflatable bladders; wherein said first pressure sensor and said second pressure sensor are configured to determine when a user has rolled over to a left-side sleeping position or to a right-side sleeping position; and wherein said processor is configured to change the inflation level to a preferred side sleeping inflation level when the user is in either the left-side sleeping position or the right-side sleeping position; and wherein said processor is configured to change the inflation level to a preferred back sleeping inflation level when the user is not in either the left-side sleeping position or the right-side sleeping position.

8. The adjustable pillow of claim 7, wherein said range of numeric settings is a range of settings between and including 1 and 25.

9. The adjustable pillow of claim 8, wherein said plurality of individually inflatable bladders positioned in said stack are each coextensive with each adjacent bladder.

10. An adjustable pillow comprising: a lower layer of foam; an upper layer of foam, a first end cap of foam; and a second end cap of foam, wherein said lower layer of foam, said upper layer of foam, said first end cap of foam, and said second end cap of foam are joined together and form a cavity therein; a plurality of individually inflatable bladders, said plurality of individually inflatable bladders positioned in said cavity; wherein each of said plurality of individually inflatable bladders has a same size and shape; wherein said plurality of individually inflatable bladders are positioned in a stack; a respective tube in fluid communication with each of said plurality of individually inflatable bladders; a pump, said pump configured, when activated, to inflate any one or more of said plurality of individually inflatable bladders to a particular pressure, to increase a height of said adjustable pillow; one or more valves, said one or more valves configured, when activated, to deflate any one or more of said plurality of individually inflatable bladders to decrease a height of said adjustable pillow; a processor and electronic circuitry configured to activate and deactivate said pump to increase the height of said adjustable pillow, and being further configured to activate and deactivate said one or more valves to decrease the height of said adjustable pillow; a communication and control module configured to control said processor to adjust inflation of said plurality of individually inflatable bladders according to a range of numeric settings, each setting corresponding to a different inflation level and corresponding height of said adjustable pillow; one or more voice activated microphones electronically coupled to said processor and electronic circuitry; wherein said communication and control module is further configured to receive a voice command received by said one or more voice activated microphones for selection of any setting from among said range of settings to adjust the inflation level and height of said adjustable pillow according to the selected setting; wherein said communication and control module is further configured to receive a voice command to assign a first setting from among said range of settings to be a side sleep position setting, and to receive a voice command to assign a second setting of said range of settings to be a back sleep position setting; wherein said communication and control module is further configured to receive a voice command of side sleep position to adjust the height of said pillow according to said first setting, and to receive a voice command of back sleep position to adjust the height of said pillow according to said second setting; wherein said communication module is further configured to receive data from an application on a mobile communication device, wherein said communication module is further configured to transmit commands from the application on the mobile communication device, to control said pump to change said inflation level; and wherein said one or more voice activated microphones are configured to receive and detect snoring sounds made by a user, said processor configured to actuate said one or more valves or actuate said pump to correspondingly deflate or further inflate said pillow to make height adjustments until the detected snoring sounds fall below a threshold level.

11. The adjustable pillow of claim 10, wherein said plurality of individually inflatable bladders comprises at least seven bladders.

12. The adjustable pillow of claim 10, wherein said lower layer of foam, said upper layer of foam, said first end cap of foam, and said second end cap of foam are formed as individual pieces of foam and joined together to form the cavity.

13. The adjustable pillow of claim 10, wherein said lower layer of foam, said upper layer of foam, said first end cap of foam, and said second end cap of foam are integrally formed as a single unitary piece of foam, with a slit into the cavity.

14. The adjustable pillow of claim 10, wherein said foam is foam from the group of foams consisting of: a memory foam; and a high expansion foam.

15. The adjustable pillow of claim 10, further comprising: a second plurality of individually inflatable bladders, said second plurality of individually inflatable bladders positioned in said cavity on a first side of said first plurality of individually inflatable bladders; a third plurality of individually inflatable bladders, said third plurality of individually inflatable bladders positioned in said cavity on a second side of said first plurality of individually inflatable bladders; a first pressure sensor positioned at said second plurality of individually inflatable bladders; a second pressure sensor positioned at said third plurality of individually inflatable bladders; wherein said first pressure sensor and said second pressure sensor are configured to determine when a user has rolled over to a left-side sleeping position or to a right-side sleeping position; and wherein said processor is configured to change the inflation level to a preferred side sleeping inflation level when the user is in either the left-side sleeping position or the right-side sleeping position; and wherein said processor is configured to change the inflation level to a preferred back sleeping inflation level when the user is not in either the left-side sleeping position or the right-side sleeping position.

16. The adjustable pillow of claim 15, wherein said range of numeric settings is a range of settings between and including 1 and 25.

17. The adjustable pillow of claim 16, wherein said plurality of individually inflatable bladders positioned in said stack are each coextensive with each adjacent bladder.

* * * * *